US010953075B2

(12) United States Patent
Morales et al.

(10) Patent No.: US 10,953,075 B2
(45) Date of Patent: *Mar. 23, 2021

(54) PHARMACEUTICAL COMPOSITIONS AND METHODS FOR FABRICATION OF SOLID MASSES COMPRISING ANTI-INTERLEUKIN ANTIBODIES

(71) Applicant: InCube Labs, LLC, San Jose, CA (US)

(72) Inventors: Mercedes Morales, San Francisco, CA (US); Mir Imran, Los Altos Hills, CA (US); Radhika Korupolu, Fremont, CA (US); Mir Hashim, Fremont, CA (US)

(73) Assignee: InCube Labs, LLC, San Jose, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 16/036,590

(22) Filed: Jul. 16, 2018

(65) Prior Publication Data

US 2019/0008925 A1    Jan. 10, 2019

Related U.S. Application Data

(63) Continuation of application No. 14/714,136, filed on May 15, 2015, now Pat. No. 10,039,810.

(60) Provisional application No. 61/993,907, filed on May 15, 2014, provisional application No. 62/156,105, filed on May 1, 2015, provisional application No. 62/159,134, filed on May 8, 2015.

(51) Int. Cl.
| | |
|---|---|
| *C07K 16/00* | (2006.01) |
| *A61K 38/28* | (2006.01) |
| *C07K 16/24* | (2006.01) |
| *A61K 9/20* | (2006.01) |
| *A61K 38/26* | (2006.01) |

(52) U.S. Cl.
CPC ............ *A61K 38/28* (2013.01); *A61K 9/2018* (2013.01); *A61K 9/2027* (2013.01); *A61K 9/2031* (2013.01); *A61K 9/2072* (2013.01); *A61K 9/2077* (2013.01); *A61K 38/26* (2013.01); *C07K 16/00* (2013.01); *C07K 16/241* (2013.01); *C07K 16/244* (2013.01); *C07K 2317/21* (2013.01); *C07K 2317/24* (2013.01); *C07K 2317/76* (2013.01)

(58) Field of Classification Search
CPC ............................ C07K 17/00; C07K 2317/21
See application file for complete search history.

(56) References Cited

U.S. PATENT DOCUMENTS

| | | | |
|---|---|---|---|
| 3,625,898 | A | 12/1971 | Ferdinand et al. |
| 8,007,768 | B1 | 8/2011 | Sung et al. |
| 8,353,863 | B2 | 1/2013 | Imran |
| 8,721,620 | B2 | 5/2014 | Imran |
| 8,759,284 | B2 | 6/2014 | Imran |
| 8,764,733 | B2 | 7/2014 | Imran |
| 8,809,269 | B2 | 8/2014 | Imran |
| 8,809,271 | B2 | 8/2014 | Imran |
| 8,846,040 | B2 | 9/2014 | Imran |
| 8,969,293 | B2 | 3/2015 | Imran |
| 8,980,822 | B2 | 3/2015 | Imran |
| 9,149,617 | B2 | 10/2015 | Imran |
| 9,283,179 | B2 | 3/2016 | Imran |
| 9,284,367 | B2 | 3/2016 | Imran |
| 10,039,810 | B2 | 8/2018 | Morales et al. |
| 10,058,595 | B2 | 8/2018 | Morales et al. |
| 10,098,931 | B2 | 10/2018 | Morales et al. |
| 10,220,076 | B2 | 3/2019 | Morales et al. |
| 2004/0195413 | A1 | 10/2004 | Reed et al. |
| 2011/0014247 | A1 | 1/2011 | Kidron |
| 2011/0046053 | A1 | 2/2011 | Kidron |
| 2011/0142889 | A1 | 6/2011 | Lee et al. |
| 2012/0053129 | A1 | 3/2012 | Park et al. |
| 2012/0128767 | A1 | 5/2012 | Lee et al. |

(Continued)

FOREIGN PATENT DOCUMENTS

| | | |
|---|---|---|
| JP | 2008509933 A | 4/2008 |
| JP | 2010502759 A | 1/2010 |

(Continued)

OTHER PUBLICATIONS

Cai, et al. Long-acting preparations of exenatide. Drug design, development and therapy 7 (2013): 963-970.
Coimbra; et al., "Brodalumab: an evidence-based review of its potential in the treatment of moderate-to-severe psoriasis. Core Evid. Jul. 21, 2014;9:89-97. doi: 10.2147/CE.S33940. eCollection 2014.".
Co-pending U.S. Appl. No. 16/050,995, filed on Jul. 31, 2018.
Co-pending U.S. Appl. No. 16/112,558, filed on Aug. 24, 2018.
European search report with written opinion dated Nov. 29, 2017 for EP Application No. EP15792136.
International search report and written opinion dated Nov. 4, 2015 for PCT/US2015/031239.

(Continued)

*Primary Examiner* — Gyan Chandra
(74) *Attorney, Agent, or Firm* — Wilson Sonsini Goodrich and Rosati, P.C.

(57) ABSTRACT

Embodiments of the invention provide shaped masses comprising one or more drugs such as proteins or polypeptides and methods for forming such shaped masses. One embodiment provides a shaped mass comprising a drug such as a protein or polypeptide having a biological activity in the body of a mammal. The shaped mass is formed by compression of a precursor material comprising the drug wherein an amount of biologically active drug in the mass is a preserved above a minimum level. Drugs which may be incorporated into the shaped mass may include one or more glucose regulating proteins such as insulin, incretins; and immunoglobulins such as TNF-inhibiting antibodies or interleukin neutralizing antibodies. Embodiments of the shaped mass may be incorporated into a tissue penetrating member which is inserted into the intestinal wall allowing for the oral delivery of proteins and peptides which would otherwise be degraded in the intestinal tract.

21 Claims, 2 Drawing Sheets

(56) References Cited

U.S. PATENT DOCUMENTS

| | | |
|---|---|---|
| 2012/0196861 A1 | 8/2012 | Leban et al. |
| 2013/0165859 A1 | 6/2013 | Imran |
| 2013/0202610 A1 | 8/2013 | Guettner et al. |
| 2013/0209480 A1 | 8/2013 | Mpofu et al. |
| 2014/0065145 A1 | 3/2014 | Debunne et al. |
| 2014/0127227 A1 | 5/2014 | Chang |
| 2014/0255406 A1 | 9/2014 | Allan et al. |
| 2015/0017238 A1 | 1/2015 | Kidron |
| 2015/0064193 A1 | 3/2015 | Wang |
| 2015/0064241 A1 | 3/2015 | Conrad |
| 2015/0328287 A1 | 11/2015 | Morales et al. |
| 2015/0329630 A1 | 11/2015 | Morales et al. |
| 2015/0329631 A1 | 11/2015 | Morales et al. |
| 2015/0329633 A1 | 11/2015 | Morales et al. |
| 2019/0008926 A1 | 1/2019 | Morales et al. |
| 2019/0015482 A1 | 1/2019 | Morales et al. |
| 2019/0275116 A1 | 9/2019 | Morales et al. |

FOREIGN PATENT DOCUMENTS

| | | |
|---|---|---|
| JP | 2013514976 A | 5/2013 |
| JP | 2013515576 A | 5/2013 |
| WO | WO-2006124047 A2 | 11/2006 |
| WO | WO-2008031770 A2 | 3/2008 |
| WO | WO-2009063222 A2 | 5/2009 |
| WO | WO-2011079302 A2 | 6/2011 |
| WO | WO-2013189988 A1 | 12/2013 |
| WO | WO-2015176031 A2 | 11/2015 |

OTHER PUBLICATIONS

Krauland, et al. Oral insulin delivery: the potential of thiolated chitosan-insulin tablets on non-diabetic rats. Journal of Controlled Release, Elsevier, Amsterdam, NL. vol. 95, No. 3, Mar. 24, 2004.
Nakanishi; et al., "Interleukin-18 is a unique cytokine that stimulates both Th1 and Th2 responses depending on its cytokine milieu. Cytokine Growth Factor Rev. Mar. 2001;12(1):53-72.".
Notice of allowance dated Apr. 6, 2018 for U.S. Appl. No. 14/714,136.
Notice of allowance dated May 3, 2018 for U.S. Appl. No. 14/714,126.
Notice of allowance dated May 17, 2018 for U.S. Appl. No. 14/714,120.
Notice of allowance dated Sep. 21, 2018 for U.S. Appl. No. 14/714,146.
Office action dated Mar. 20, 2018 for U.S. Appl. No. 14/714,146.
Office action dated Apr. 26, 2017 for U.S. Appl. No. 14/714,136.
Office action dated May 9, 2017 for U.S. Appl. No. 14/714,120.
Office action dated May 9, 2017 for U.S. Appl. No. 14/714,126.
Office action dated May 9, 2017 for U.S. Appl. No. 14/714,146.
Office action dated Jul. 28, 2016 for U.S. Appl. No. 14/714,136.
Office action dated Aug. 11, 2016 for U.S. Appl. No. 14/714,120.
Office action dated Sep. 12, 2016 for U.S. Appl. No. 14/714,126.
Office action dated Sep. 15, 2016 for U.S. Appl. No. 14/714,146.
Notice of allowance dated Oct. 24, 2018 for U.S. Appl. No. 14/714,146.
Marschütz, et al. Design and in Vivo Evaluation of an Oral Delivery System for Insulin. Pharm Res. Dec. 2000;17(12):1468-1474. doi: 10.1023/a:1007696723125.
Office action dated Jun. 11, 2020 for U.S. Appl. No. 16/229,711.

PHARMACEUTICAL COMPOSITIONS AND METHODS FOR FABRICATION OF SOLID MASSES COMPRISING ANTI-INTERLEUKIN ANTIBODIES

CROSS-REFERENCE TO RELATED APPLICATIONS

This application is a continuation of U.S. patent application Ser. No. 14/714,136, filed May 15, 2015, now U.S. Pat. No. 10,039,810; which claims the benefit of priority of U.S. Provisional Patent Application Ser. No. 61/993,907, filed May 15, 2014; U.S. Provisional Patent Application Ser. No. 62/156,105, filed May 1, 2015; and U.S. Provisional Patent Application Ser. No. 62/159,134, filed May 8, 2015; all of which are fully incorporated herein by reference.

FIELD OF THE INVENTION

Embodiments described herein relate to pharmaceutical compositions and methods of fabrication of pharmaceutical compositions comprising solid masses comprising proteins and polypeptides. More specifically, embodiments described herein relate to pharmaceutical compositions and methods of production of pharmaceutical compositions comprising solid shaped masses comprising proteins and/or polypeptides having a biological activity wherein at least a portion of the biological activity of the protein or polypeptide is maintained after formation of the solid mass.

BACKGROUND

While there has been an increasing development of new drugs in recent years for the treatment of a variety of diseases, many including proteins, antibodies and peptides have limited application because they cannot be given readily formed into solid shapes for oral or other form of delivery and/or encapsulated. One challenge in this area is that the process of fabrication of a drug comprising a protein, peptide or antibody into tablet or other solid form can result in loss in the bioactivity of the drug due to disruption of the structure of the protein from the fabrication process. This is due to the fact that many proteins have complex internal structures that define their biological activity. Disruption in the structure of a protein and/or polypeptide can result in its deactivation or considerable decline of its bioactivity. Such disruption can result from fabrications processes such as molding, compression, milling, grinding or encapsulation or other related process. What is needed is a method for forming bioactive compounds such as proteins, antibodies and peptides into solid or semi-solid shapes for oral or other form of delivery to a human or other mammal without significant loss of bioactivity of the compound.

BRIEF SUMMARY OF THE INVENTION

Various embodiments of the invention provide pharmaceutical compositions comprising solid shaped masses including one more or more drugs and methods of production of the shaped masses. The drug may comprise one or more polypeptides or proteins such as various immunoglobulins. Many embodiments provide methods for forming solid shaped masses comprising one or more proteins or polypeptides where the shaped masses are formed by the shaping of a precursor material and where at least a portion of the biological activity of the protein or polypeptide in the shaped mass is preserved after formation. In many embodiments, the shaping is done by compression of the precursor material where the compressive forces are selected to minimize degradation of the biological activity of the protein or polypeptide. Other shaping methods are also contemplated. Typically, the precursor material will comprise a powder mixture comprising the drug and one or more excipients. The precursor material may also comprise a liquid, slurry or paste. The excipients may include one more of a lubricant, a binder, bulking agent, etc. The shaped mass may be in the form of a tablet, micro-tablet, pill or slug shape. According to one or more embodiments, the shaped masses produced using embodiments of the formation process can have another property such as density or particle grain size (of the powder used to formulate the shaped mass) which is correlated to minimum level of bioactivity of the protein or peptide. Also, that correlated property may be may consistently maintained within a selected range within a given lot of shaped masses as well from lot to lot. Embodiments of the solid masses described herein can be configured to be used in combination with any suitable drug delivery system to be administered via any appropriate route of administration for the condition to be treated. Such routes of administration can include without limitation, oral, sublingual parenteral, intra-venous, intramuscular, intra-ventricular, intra-cardiac. For example, according to one embodiment, insulin containing micro-tablets can be taken orally and delivered into the small intestine where the drug is delivered into the wall of the of the small intestine where the tablet(s) dissolves to release the drug into the blood stream. In another embodiment, insulin containing micro tablets can be injected or otherwise placed subcutaneously (e.g. intramuscularly) where they dissolve to release insulin into the bloodstream.

In one aspect, the invention provides pharmaceutical compositions comprising solid shaped masses comprising a drug or other therapeutic agent having a biological activity in the body of a mammal wherein at least a portion of the biological activity of the drug is maintained after formation from a precursor material such as powder. The biological activity may be correlated to the structural integrity of the drug post formation (e.g. by correlating bioactivity assays to chemical assays), such that on a compositional level, a selected percentage of the drug (e.g., on a weight basis) is maintained post formation relative to that in the precursor material. Typically, the shape will be formed by a compression process (e.g. compression molding), though other processes are also contemplated such as non compressive molding. The drug may comprise a protein, peptide or antibody wherein the biological activity of the drug in the shaped mass is at least 70% to that prior to compression and more preferably, at least 90% to that prior to compression and still more preferably at least 95%. These numbers may also correspond to a weight percentage of the drug remaining in the shaped mass relative to that in the precursor material (e.g., by correlating biological activity assays to chemical assays for weight composition as described above). In these and related embodiments, the shaped mass can have a density in a range of about 1.00 and 1.15 mg/mm$^3$ and in more preferred embodiments, 1.02 and 1.06 mg/mm$^3$. The shape will typically comprise a pellet shape but may also have a tablet, conical, cylindrical, cube, sphere or other like shape.

According to various embodiments, in addition to the drug and other excipients, the shaped mass can be formed from a biodegradable material that is configured to dissolve or otherwise degrade in the wall of the intestine such as the small intestine (or another tissue site, e.g. an intramuscular site) so as to release the drug into the intestinal wall where it diffuses or otherwise is transported into the capillary bed of the intestinal wall and then is carried by the circulatory system throughout the body. The shaped mass may inserted or otherwise incorporated into a structure, such as a tissue penetrating member that is made from such a biodegradable material. The tissue penetrating member being configured to be penetrate and be inserted into the wall of the small intestine (or other lumen in the GI tract) by the application of force on the tissue penetrating member. Suitable biodegradable materials include various sugars such as maltose and sucrose, various lactic acid polymers such as polyglycolic acid (PGA), polylactic acid (PLA); polyglycolic lactic acid (PGLA); various polyethylenes, various celluloses, such as HPMC (hydroxypropyl methyl cellulose), PVOH (polyvinyl alcohol), silicone rubber. and other biodegradable polymers known in the art. The material and other properties of the degradable polymer and shaped mass can be selected to produce selectable rates of degradation in the intestinal wall. According to one or more embodiments the rates of degradation can be selected to achieve various pharmacokinetic parameters such as $t_{max}$, $C_{max}$, $t\ ½$, etc. In one more specific embodiments, the materials properties of the shaped mass can be selected so as to have the shaped mass degrade within the intestinal wall to achieve a $C_{max}$ for the selected drug(s) in a shorter time period than a time period to achieve a $C_{max}$ for an extravascularly injected dose of the drug.

In one embodiment, the drug in the shaped mass comprises a glucose regulating protein such as insulin for the treatment of diabetes or other glucose regulation disorder. The insulin may be obtained from any suitable source (e.g. human insulin and/or that generated using recombinant DNA methods). In another application, the drug comprises a glucose regulating protein such as an incretin (e.g., exenatide) for the treatment of a glucose regulation disorder. In these and related embodiments the compression or other molding process is configured to preserve the biological activity of the insulin or incretin or other glucose regulating protein so as to be able to allow the drug to treat diabetes or other glucose regulation disorder once released into the body of a patient.

Still other embodiments provide shaped masses and methods for their fabrication wherein the drug or other therapeutic agent in the shaped mass comprises an antibody such as IgG or an antibody from the TNF inhibiting class of antibodies such as adalimumab (HUMIRA), infliximab (Remicade), certolizumab, pegol (Cimzia), golimumab (Simponi), or etanercept (Enbrel) wherein the biological activity of the anti-body is preserved after formation of the shaped mass in amounts of about 70, 75, 80, 85, 90 or 95% relative to that of a precursor material prior to formation.

Yet still other embodiments provide shaped masses and methods for their fabrication methods wherein the drug comprises an interleukin neutralizing protein such as an antibody which binds to one more or interleukins or their receptors wherein the biological activity of the anti-body is preserved after formation of the shaped mass in amounts of 70, 75, 80, 85, 90 or 95% relative to that of a precursor material prior to formation. Such interleukins can include one more of interleukins 1-36 (e.g. interleukin 1, interleukin 17a) and their respective analogues and derivatives. The interleukin neutralizing proteins are also referred to herein as IN proteins (and also as an interleukin binding protein or IB-protein), the anti-interleukin antibodies are referred to herein as AI-antibodies and antibodies to the interleukin-17 family of antibodies as AI17-antibodies. The AI antibody or other IN protein is capable of neutralizing and/or inhibiting the biologic effects of one more of interleukins 1-36 by preventing or diminishing the ability of the selected interleukin from binding to a receptor for that interleukin.

Such a neutralizing effect produced by a particular IB-protein can be achieved by selecting the IB-protein to either: 1) bind to the selected interleukin so as prevent or inhibit that interleukin from binding to the receptor for that interleukin and in turn causing one or more biological effects; or 2) bind to a receptor for that particular interleukin so as to prevent the interleukin from activating the receptor and causing the one or more biologic effects. For example, according to one embodiment, an antibody such as Secukinumab can be selected which binds to interleukin-17. According to other embodiments, an antibody such as Brodalumab can be selected which binds to the receptor for interleukin 17. The inhibited biological effects resulting from use of one or more embodiments of shaped masses comprising AI-antibodies or other IB-proteins can include one or more of the following: Th1 modulation; Th2 modulation (Nakanishi K., et al. (2001) Cytokine and Growth Factor Rev. 12:53-72); Nk modulation; neutrophil modulation; monocyte-macrophage lineage modulation; neutrophil modulation; eosinophil modulation; B-cells modulation; cytokine modulation; chemokine modulation; adhesion molecule modulation; and cell recruitment modulation. Also, according to one or more embodiments, the AI-antibody or other IN-protein can be selected to inhibit the biologic effects of a selected interleukin so as to treat a variety of autoimmune and/or inflammatory conditions associated with the activity of the selected interleukin. In preferred embodiments, such conditions can include one more of rheumatoid arthritis, psoriasis including plaque psoriasis, psoriatic arthritis, fibrosis, ulcerative colitis, Crohn's disease, inflammatory bowel disease, multiple sclerosis and ankylosing spondylitis.

The IN-protein incorporated into the shaped mass may be selected from an immunoglobulin molecule such as an antibody or functional variants thereof known in the art, with such variants retaining the characteristic binding property of the interleukin binding protein. The immunoglobulin may correspond to a full-length antibodies or an antigen-binding portion thereof. Examples of specific immunoglobulin molecules which may be used include but are not limited to an scFv (single chain variable fragment); a monoclonal antibody; a human antibody; a chimeric antibody; a humanized antibody; a single domain antibody; a Fab fragment; an Fab' fragment; an F(ab')2; an Fv (variable fragment); a disulfide linked Fv, and a bi-specific or dual specific antibody. Most preferably, the binding protein is a human antibody.

In many embodiments the dose of the selected AI-antibody, AI-17 antibody or other IN-protein formulated into and/or as the shaped mass can be titrated to treat a selected condition described herein (e.g. psoriasis, rheumatoid arthritis, etc.), while minimizing the adverse effect associated with an injected dose (e.g. intravenous, intramuscular, subcutaneous etc.) of the antibody. Such adverse effects can include without limitation one or more of anaphylactic shock or other allergic reaction (e.g., edema, water eyes, respiratory congestion), immunogenic reaction to the IN-protein (including immunogenic neutralization of the delivered IN-protein by patients own antibodies), headache, fever and other related effect. In particular embodiments, this can be achieved by titrating the delivered dose of AI-antibody or other IN-protein to a daily vs a monthly dose which is typically given for AI-antibodies such as that for Secukinumab, Brodalumab or Ixekizumab. For the case of minimizing immune response, this result can also be achieved by delivering the dose of AI-antibodies to the upper or mid portion of the small intestine and avoiding the lower section of the intestine e.g., the ileum containing the Peyer's patches as is discussed in further detail herein. Other benefits of delivering the AI-antibody in smaller doses into the small intestine (vs by injection) include one or more of i) higher therapeutic ratios; and ii) reduced fluctuation in the plasma concentration for the AI-antibody or other IN protein.

Still other embodiments provide methods of preparing a shaped mass comprising a drug wherein an outer coating or layer is formed over the drug using 3-D printing methods so as to produce a selectively shaped mass. Use of 3-D printing methods allow the shaped mass to be formed without the application of pressure on the mass. In use, such methods improve the yield of the drug in the final shaped mass due to decreased protein denaturation and/or other degradative effects on the drug. This in turn improves the bioactivity of the drug in the final shaped mass. Use of 3-D printing also allows a variety of shapes to be produced without use of a mold or other related device reducing the potential for contamination and improving sterility. Such shapes may include for example, an arrow head shape, rectangle, pyramidal, spherical, hemispherical, conical and others. 3-D printing methods also allow for rapid customization of the drug mass shape and size for individual patient parameters, for example one or more of a patient's weight, medical condition and particular medical regimen (e.g. taking of medication once daily, twice etc.). In still other embodiments, 3-D printing methods can be used to produce shaped masses configured to have a bimodal form of delivery, e.g. fast release and slow release.

Other embodiments provide an inventory comprising a plurality of shaped masses of a pharmaceutical composition comprising a drug such as a peptide, protein or immunoglobulin, wherein a property of the shaped mass, such as the biological activity of the drug after formation and/or density of the shaped mass, is maintained within a selected range for substantially the entire inventory. In use, such embodiments provide for the ability to maintain uniform dosage and pharmacokinetic parameters for one or more selected drugs delivered using embodiments of the shaped masses described herein.

Further details of these and other embodiments and aspects of the invention are described more fully below with reference to the accompanying figures.

BRIEF DESCRIPTION OF THE DRAWINGS

FIG. 1b is a perspective view of the embodiment of FIG. 1a.

DETAILED DESCRIPTION OF THE INVENTION

Figure 1A:
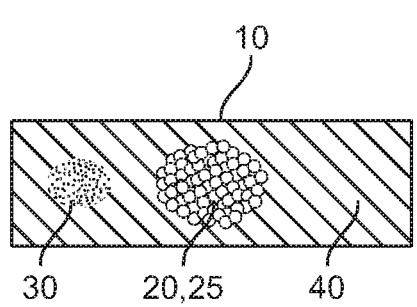
FIG. 1a is a lateral cross sectional view showing an embodiment of the shaped mass having a cylindrical shape.
Figure 1B:
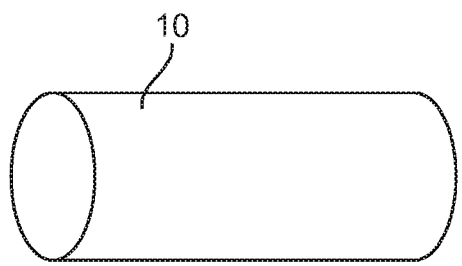
Figure 2:
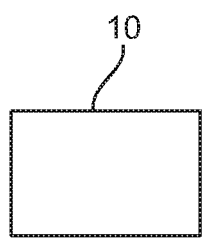
FIG. 2 is a lateral view showing an embodiment of the shaped mass having a cubical shape.
Figure 3:
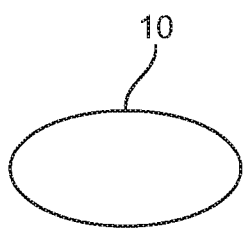
FIG. 3 is a lateral view showing an embodiment of the shaped mass having a hotdog/capsule like shape.
Figure 4:
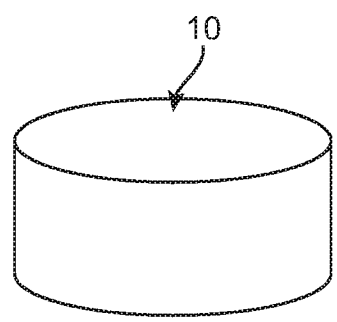
FIG. 4 is a lateral view showing an embodiment of the shaped mass having a tablet shape.
Figure 5:
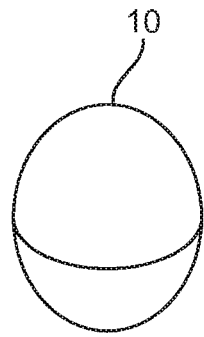
FIG. 5 is a perspective view showing an embodiment of the shaped mass having a spherical shape.
Figure 6:
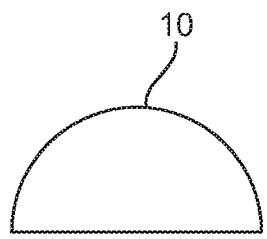
FIG. 6 is a lateral view showing an embodiment of the shaped mass having a hemispherical shape.
Figure 7:
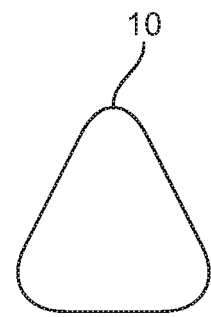
FIG. 7 is a lateral view showing an embodiment of the shaped mass having a pyramidal shape.
Figure 8:
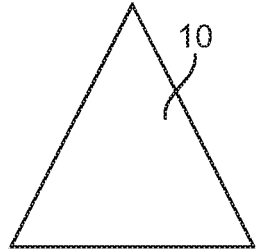
FIG. 8 is a lateral view showing an embodiment of the shaped mass having an arrow-head shape.
Figure 9:
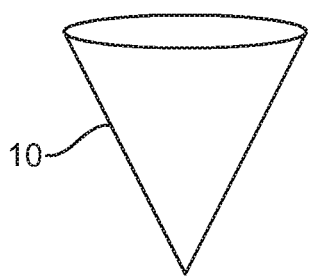
FIG. 9 is a perspective view showing an embodiment of the shaped mass having a conical shape.
Figure 10:
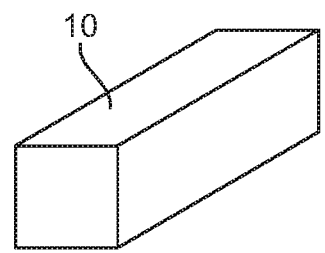
FIG. 10 is a perspective view showing an embodiment of the shaped mass having a rectangular shape.

With reference now to FIGS. 1-10, various embodiments of the invention provide pharmaceutical compositions in the form of solid shaped masses 10 comprising one more drugs and methods for forming solid shaped masses comprising one or more drugs. According to one or more embodiments, the drug may comprise one or more polypeptides and proteins such as various immunoglobulins proteins (e.g. an antibody) which have a biological activity (e.g. binding affinity for an antigen) which may be decreased by conventional solid pharmaceutical formulation processes (e.g., such as various compression processes used to form pills, tablets etc.) which degrade or otherwise damage the molecular structure of the protein or peptide. One embodiment of the shaped mass 10 is shown in FIGS. 1a and 1b comprises a therapeutic composition 20 which can include one or more drugs or other therapeutic agents 25; an excipient 30 and a degradable material 40 (such as polyethylene, various sugars, lactic acid polymer, PGLG, etc.) which degrades within a target delivery site in the body (e.g., the wall of the small intestine) to release drug 25.

The shaped mass can 10 be formed from a variety of shaping processes known in the pharmaceutical arts. Typically, the shaped mass will be formed by a compression process such as compression molding. The drug may comprise a protein, peptide or antibody. According to one or more embodiments, the biological activity of the protein or peptide in the mass is at least about 70% to that prior to compression, more preferably, at least 80% to that prior to compression, more preferably, at least 85% to that prior to compression, still more preferably about 90% to that prior to compression and still more preferably at least 95% prior to compression (as used herein the term "about" means within 2% and more preferably within 1% of the stated value). These numbers may also correspond to a percentage (e.g. by weight) of the drug in the shaped mass relative to that prior to formation. In these and related embodiments, the shaped mass can have a density in a range of about 0.80 to about 1.15 mg/mm$^3$, more preferably in a range from about 0.90 to about 1.10 mg/mm$^3$, still more preferably in a range of about 1.02 to 1.06 mg/mm$^3$ and still more preferably in a range from about 1.03 to 1.05 mg/mm$^3$. The shape of the shaped mass will typically comprise a pellet shape but may also have a tablet, conical, pyramidal, hot dog/capsule like, arrow head, cylindrical, cube, sphere, hemisphere or other like shape as is shown in FIGS. 1-10. Also in these or alternative embodiments, the particle size (e.g. diameter or widest dimension) of the powder used to make the shape mass 10 may be in the range of about 50 to 450 μm, more preferably between about 100 to 400 μm and still more preferably between about 200 to 400 μm with other ranges also contemplated. For embodiments of the shaped mass having a cylindrical or pellet shape, the shaped mass may have a diameter in the range from about 0.5 to 1 mm and a length from about 1.75 to 3.25 mm.

According to various embodiments, the shaped mass 10 can be formed in part from a degradable material 30 that is configured to dissolve or otherwise degrade in the wall of the intestine such as the small intestine (or another tissue site, e.g. an intramuscular site) so as to release the drug into the intestinal wall where it diffuses or otherwise is transported into the capillary bed of the intestinal wall and then is carried by the circulatory system throughout the body. As used herein the term degrade includes one more of the processes of biodegradation, dissolving or disintegration due to contact with a biological fluid (e.g., blood, interstitial fluid, lymph etc.) and/or tissue. Also the terms degrade and degradation can be used interchangeably. Suitable degradable materials 30 include various sugars such as maltose and sucrose, various lactic acids polymers such as polyglycolic acid (PGA), polylactic acid (PLA); polyglycolic lactic acid (PGLA); various polyethylenes such as high density, low density and linear low density PE and PEO (polyethylene oxide), various cellulose polymers such as HPMC (hydroxypropyl methyl cellulose), CMC (carboxy methyl cellulose), MC (methyl cellulose), methacrylic acid-ethyl acrylate copolymer, methacrylic acid-methyl methacrylate copolymer PVOH (polyvinyl alcohol), silicone rubber. and other biodegradable polymers known in the art. The material and other properties of the degradable polymer and shaped mass can be selected to produce selectable rates of degradation in the intestinal wall. According to one or more embodiments, the rates of degradation can be selected to achieve various pharmacokinetic parameters such as $t_{max}$, $C_{max}$, $t$ ½, etc. In one or more specific embodiments, the materials properties of the shaped mass (e.g. its chemical composition, solubility in interstitial fluids, size and shape) can be selected so as to have the shaped mass degrade within the intestinal wall to achieve a $C_{max}$ for the selected drug(s) in a shorter time period than a time period to achieve a $C_{max}$ for an extravascularly injected dose of the drug.

Embodiments of Methods for Fabricating Drug Containing Shaped Masses.

A description will now be provided of the fabrication process used to make various embodiments of the drug containing shaped masses described herein. The process includes a process for fabricating a powder containing one or more drugs and a shaped mass formation process for forming the powder into microtablets or other shaped masses comprising one or more drugs. For ease of discussion, the shaped masses will now be referred to as microtablets; however it should be appreciated that other forms and/or shapes for the shaped masses are equally applicable (e.g., pellet, cylindrical, hot dog like shape, etc).

Drug Powder Formation Process.

The process for formulation of a powder comprising the drug will now be described. Typically, it includes three steps. The first step is to prepare an aqueous solution of the drug and then add the desired excipients 30 for the particular application. According to one or more embodiments, excipients 30 can include one or more of a lubricant, a binder and a bulking agent. The lubricant is added to facilitate both microtablet formation and ejection from a mold. The lubricant may correspond to polyethylene glycol 3350 and in one or more embodiments, may be added in proportion of approximately 10% w/w of the total batch mass. The bulking agent may correspond to mannitol and the binder may correspond to povidone. Other excipients which may be added include binders, fillers, disintegrats, stabilizers, buffers and antimicrobials. The proportions of the different ingredients, active and non-active, in the powder mixture are taken into consideration during the formulation process so as to achieve a desired therapeutic dose of the drug in the resulting microtablet.

The second step is to evaporate the aqueous mixture. The gently-mixed solution containing the drug and the excipients is then placed in a flexible and flat plate (for example, silicone plate) inside of a vacuum chamber containing desiccant. The chamber is then placed inside of a refrigerator or cold room and is connected to a vacuum line or pump. The solution is left under vacuum and low temperature, above 0° C., until it dries out completely.

The third step comprises milling the evaporated mixture to produce a fine powder. The evaporated mixture is placed in a low-protein-binding tube along with a single high-density milling ball, preferably, made of stainless steel or yttrium-stabilized zirconium. The milling is done using a rotator at max speed containing the tube film-wrapped to avoid moisture absorption or contamination. An ice pack is desirably placed on top of the tube to keep it cold. The room temperature can be controlled in a range for example from 60 to 64° F. The size of the milling tube, mass of the milling ball and duration of mixing may be selected to produce particular powder grain sizes, grain size homogeneity and powder density. For example, for the production of a 40 mg to 100 mg batch capacity, the use of a bottom-rounded 2 mL tube, a milling ball having a 0.44 g mass and a milling duration of 3 hours resulted in fine and consistent grain sizes, achieving more homogeneous and reliable density values.

Microtablet Fabrication Process.

In various embodiments, the microtablet fabrication process is desirably (though not necessarily) done in a clean and temperature-controlled room where the temperature is kept between 60-64° F. The microtablet formation process is typically done via compression using a compression mold or other fixture to apply a compressive force to the powder including the drug. Two types of compression fixtures may be used, a semiautomatic one or a fully automatic version. For fabrication using the semiautomatic fixture, the microtablets are fabricated over a base which consists of two metal sheets connected to a force gauge stand by four cylinders, four springs and four vibration mounting stoppers. The top sheet has a cavity with a hole on it for a mold or well to slide in. The mold used for the compression has a 45 degree funnel ending in a well with required diameter and length to accommodate the powder for compression. A pin is attached to a pin holder and connected to the force gauge which can be moved up and down by a controlled motor operated by a 3-way switch.

The semiautomatic fabrication procedure can include the following steps: 1) positioning of a stopper, 2) placing a tablet mold on top of the stopper and a pin into the holder, 3) loading the powder required for the microtablet and letting it sink/settle into the mold hole, 4) compressing the powder into the mold by advancing a motorized pin (which is connected to force gauge) into the mold until a desired force is reach (i.e. compression force) and holding it in position with the applied force for a set time period (i.e. hold time), 6) removing the tablet metal stopper and place a dish to collect the tablet, and 7) lowering the pin with the motor switch until the micro-tablet exits the mold and collecting the microtablet in a dish. The combination of compression force and hold time will determine the mechanical structure of the microtablet as well as the decrease in the bioactivity of the drug.

For the process using the automatic fixture, the processes of drug sinking, compression and ejection are fully automated. The mold rests in a base and is restrained by a mold holder by three screws. The mold bottom is in contact with a piece of metal referred to as a "gate" which can be move by the action of an air cylinder. The gate will stop the powder from falling down during loading and compression and will open during the ejection. An air cylinder is attached to the force gauge stand by a cylinder holder. This top air cylinder has a pin holder attached to its piston rod with a pin in it, which has the diameter required to be inserted into the mold hole and compress the powder. In general, a diameter of 0.0005" less than the diameter of the mold hole would be enough to have a tight fit between pin and mold hole. The top air cylinder connected to the pin extends to produce the powder compression and the ejection of the microtablet. A reed switch is connected to this cylinder to know the position of the piston rod. The stand also has a pneumatic vibrator with an air filter to vibrate the system and force the powder to move inside of the mold hole during loading. The three pneumatic components, gate air cylinder, compression/ejection top air cylinder and vibrator, are controlled by an electro-pneumatic system. This system consists of a power supply, programmable logic controller (PLC), four solenoids valves, reed switch, foot-switch pedal and a control panel that includes four regulators, four pressure gauges, micrographic panel and power switch.

In an automated embodiments for fabrication of the shaped mass, the controlling system may be built and programmed in a way for the user to complete the following sequence: 1) user loads the powder; 2) user presses the pedal for initiation and hold it until the end of the sequence; 3) vibration starts (vibration duration and pressure can be modified at control panel); 4) powder is compressed by the pin due to the extension of the top cylinder (compression duration and pressure can be modified at control panel) followed by the retraction of the cylinder after compression; 5) gate is opened by the retraction gate air cylinder (gate pressure can be modified at control panel as well as the time for opening and closing the gate); 6) the microtablet is ejected by the new extension of top air cylinder (ejection duration and pressure can be modified at control panel) followed by the retraction of the cylinder after ejection; finally 7) the gate closes ending the sequence.

After the micro-tablet is fabricated, the length, weight, density and bioactivity of the drug in the pellet are measured. The bioactivity of the drug in the micro-tablet may be assayed using an Enzyme-linked immunosorbent assay (ELISA) or other immune assay known in the art.

Embodiments of Shaped Masses Comprising Insulin.

According to one or more embodiments of the pharmaceutical compositions described herein, the drug contained in the microtablet or other shaped mass comprises insulin or like molecule for the treatment of diabetes or other glucose regulation disorder. The insulin may be obtained from any suitable source e.g. human insulin and/or that generated using recombinant DNA methods known in the art. The specific dose of the insulin contained in the mass can be selected based on one more of the weight, age and other parameter of the patient. In specific embodiments, the microtablet may comprise between about 0.2 to about 0.8 mg of insulin In various embodiments, the shaped mass may be formed according to one more methods described herein including compression forming methods/processes such as those described in the examples. In these and related embodiments, the compression forming method is configured to preserve the biological activity of the insulin in the microtablet so as to be able to allow the drug to treat diabetes or other glucose regulation disorder once released into the body of a patient. The compression force use in such compression methods may be in the range of about 1.5 to 3 pounds of force. The weight percent of the insulin in the mass can range from about 10 to 95%, more preferably from about 20 to 95%, still more preferably from about 25 to 95% and still more preferably from about 80 to 95%. The biological activity and/or weight percentage of the insulin in the shaped mass may be in a range from about 88 to 99.8% to that prior to formation (e.g. from a powder use to form the microtablet). The density of the microtablet in such embodiments can range from about 0.95 to about 1.15 mg/mm$^3$, more preferably from about 1.0 to about 1.10 mg/mm$^3$. In preferred embodiments, the biological activity of the insulin in the shaped mass may comprise 99.2 to 99.8% of that prior to formation. The density of the microtablet in such embodiments can range from about 1.08 to 1.10 mg/mm$^3$. Measurement of the biological activity of the insulin in the shaped mass can be performed using assays known in the art, including ELISA or other immuno-assay methods.

According to one or more embodiments, the insulin containing shaped mass may also comprise one or more excipients including, for example, a lubricant, a bulking agent and a binding agent or binder. The lubricant is selected to reduce the amount of force required to eject drug containing shaped masses from a mold and may correspond to polyethylene glycol (PEG) an example including PEG 3350. The bulking agent may correspond to mannitol and the binder may correspond to povidone. The weight percent of the insulin in the mass can range from about 10 to 95%, more preferably from about 20 to 95%, still more preferably from about 25 to 95% and still more preferably from about 80 to 95%. The weight percent of PEG can range from about 1 to 10% with a specific embodiment of 5%. The weight percent of Mannitol can range from about 4 to 70% with a specific amount of 5%. The weight percent of Povidone can range from about 1 to 5% with a specific embodiment of 1%.

Embodiments of Shaped Masses Comprising Incretin.

According to one or more embodiments of the pharmaceutical compositions described herein, the drug contained in the micro-tablet or other shaped mass comprises an incretin such as exenatide for the treatment of a glucose regulation disorder such as diabetes. Other incretins are also contemplated. The shaped mass may be formed according to one more methods described herein including compression forming methods such as those described in the examples for insulin. As described above for insulin the compression forming method is configured to preserve the biological activity of the incretin in the microtablet so as to be able to allow the drug to treat diabetes or other glucose regulation disorder once released into the body of a patient. The specific dose of the exenatide or other incretin contained in the mass can be selected based on one more of the weight, age and other parameter of the patient. In specific embodiments, the microtablet may comprise between about 0.2 to about 1 to 5 mgms of exenatide. The density of the mass containing the incretin can be in the range of 1.04±0.10 mg.

Embodiments of Shaped Masses Comprising TNF Inhibiting Antibody.

According to one or more embodiments of the pharmaceutical compositions described herein, the drug contained in the micro-tablet or other shaped mass comprises an antibody from the TNF (Tumor Necrosis Factor) inhibitor class of antibodies (e.g., adalimumab) for the treatment of various autoimmune disorders (e.g. rheumatoid arthritis, etc) which are characterized by the over production of tissue necrosis factor. In these and related embodiments, the compression and other aspects of the forming process used to fabricate the microtablet or other shaped mass is configured to preserve the biological activity of the TNF inhibiting antibody so as to be able to treat one or more autoimmune disorders including but not limited to Rheumatoid arthritis, Psoriatic arthritis, ankylosing Crohn's disease, ulcerative colitis, plaque psoriasis and juvenile idiopathic arthritis In specific embodiments, the TNF inhibiting antibody contained in the microtablet or other shaped mass may correspond to one or more of adalimumab (HUMIRA), infliximab (REMICADE), certolizumab pegol (CIMZIA) or golimumab (SIMPONI), or etanercept (ENBREL) to treat in therapeutic doses to treat one or more of the aforementioned or other conditions.

As various embodiments of the shaped masses described herein comprise TNF antibodies, a brief discussion will now be presented on the TNF inhibitor class of antibodies, the conditions they treat and the mechanism of treatment. Tumor necrosis factor (TNF, or TNF-α) is a cytokine involved in systemic inflammation. The primary role of TNF is in the regulation of immune cells. TNF, being an endogenous pyrogen, is able to induce fever, to induce apoptotic cell death, to induce sepsis (through IL-1 & IL-6 production), to induce cachexia, induce inflammation, and to inhibit tumorigenesis and viral replication. TNF promotes inflammatory response, which in turn causes many of the clinical problems associated with autoimmune disorders such as rheumatoid arthritis, spondylitis, Crohn's disease, psoriasis, hidradenitis suppurativa and refractory asthma. Antibodies that can therapeutically achieve inhibition of TNF-α come under this TNF α (Tumor Necrosis Factor α) inhibitor class of antibodies. All antibodies including this TNFα inhibitory class of antibodies are characterized by having the structure of antibody, which is described as containing two fragments, Fab and Fc, joined together by disulphide bonds to form a Y-shaped molecule. Examples for the TNFα inhibitory class of antibodies include: Infliximab (Remicade) a mouse Fab-human Fc chimeric antibody (~150 kda); Adalimumab (HUMIRA) ~148 kda, a fully humanized antibody; Etanercept (Enbrel) 1~50 kda, p75 TNF-receptor domain-Fc (IgG1) fusion protein; and Certolizumab pegol (Cimzia) which has human mab (Fab) linked to PEG. The most labile part of an antibody including the TNFα inhibitory class of antibodies is the disulphide bonds at the junction of the Y-shape. As shown by the examples herein, the inventors have demonstrated (by virtue of ELISA data showing that antibody molecule remain structurally intact and retains its bioactivity) that these disulphide bonds are preserved for various antibodies incorporated into a microtablet fabricated using the compression formation methods described herein. Therefore, one skilled in the art will appreciate that embodiments of the compression formation methods described herein would be expected to preserve the structure and bioactivity of antibody (including the TNF inhibitory class of antibodies) which has disulphide bonds at the junction of its Y-shaped molecule.

A description of the formation process for a microtablet or other shaped mass comprising adalimumab (herein HUMIRA), will now be provided; however it should be appreciated that this process is applicable to any antibody and in particular to any antibody in the TNF inhibitory class of antibodies (e.g., infliximab or etanercept, etc.) or in the AI or AI17 class of antibodies. The compression force used to fabricate a microtablet containing HUMIRA may in the range of 1.0 to 4 pounds of force, with a specific embodiment of 3 lbs. The weight percent of the HUMIRA in the mass can be in a range from about 60 to 95%, more preferably, from about 80 to 95%, with a specific embodiment of about 95%. The biological activity of the HUMIRA in the shaped mass may be in a range from about 67 to 99% to that prior to formation (e.g. from a powder used to form the microtablet). The density of the microtablet in such embodiments can range from about 0.86 to 1.05 mg/mm$^3$, more preferably from about 0.88 to about 1.03 mg/mm$^3$. In preferred embodiments, the biological activity of the HUMIRA in the shaped mass may comprise 86 to 99% of that prior to formation. The density of the microtablet in such embodiments can range from about 1.09 to 1.17 mg/mm$^3$. Measurement of the biological activity of the HUMIRA in the shaped mass can be performed using assays known in the art, including ELISA or other immuno-assay methods.

According to one or more embodiments, the HUMIRA containing shaped mass may also comprise one or more excipients 30 including, for example, a lubricant, a bulking agent and a binding agent or binder. The lubricant is selected to reduce the amount of force required to eject drug containing shaped masses from a mold and may correspond to polyethylene glycol (PEG) an example including PEG 3350. The bulking agent may correspond to mannitol and the binder may correspond to povidone. The weight percent of PEG can range from about 1 to 15% with a specific embodiment of 10%. In various embodiments of the shaped masses used to treat immune conditions such as rheumatoid arthritis, the final dose of HUMIRA in the shaped mass can be in a range of about 1 to 4 mgs, with a specific embodiments of 1.3 mgs for a once a day daily dose so as to correspond to a monthly injected dose of 40 mgs.

Embodiments of Shaped Masses Comprising Anti-Interleukin Antibodies

According to various embodiments, the drug contained in the micro-tablet or other shaped mass comprise may comprise antibodies or other binding proteins which attenuate the biological effects of one or more members of the interleukin family by either binding to a particular interleukin or the receptors for that interleukin so as to prevent in either case the interleukin from attaching to the receptor for that interleukin. Interleukins are a group of cytokines (both secreted proteins and signaling molecules) which play an important role in the immune system both as signaling molecules and secreted proteins involved in the humoral and cellular responses of the immune system. For the IL-17 family of cytokines in particular, numerous immune regulatory functions have been reported presumably due to their induction of many immune signaling molecules. The most notable role of IL-17 is its involvement in inducing and mediating pro-inflammatory responses. IL-17 is commonly associated with allergic responses. IL-17 induces the production of many other cytokines (such as IL-6, G-CSF, GM-CSF, IL-1β, TGF-β, TNF-α), chemokines (including IL-8, GRO-α, and MCP-1), and prostaglandins (e.g., PGE2) from many cell types (fibroblasts, endothelial cells, epithelial cells, keratinocytes, and macrophages). The release of cytokines causes many functions, such as airway remodeling, a characteristic of IL-17 responses. The increased expression of chemokines attracts other cells including neutrophils but not eosinophils. IL-17 function is also essential to a subset of CD4+ T-Cells called T helper 17 (Th17) cells. As a result of these roles, the IL-17 family has been linked to many immune/autoimmune related diseases including rheumatoid arthritis, psoriasis, psoriatic arthritis, inflammatory bowel disease, ulcerative colitis, lupus, allograft rejection and anti-tumor immunity.

According to various embodiments, such anti-interleukin antibodies herein, AI-antibodies, may correspond to a full-length antibody or an antigen-binding portion thereof. Also, they will typically though not necessarily, comprise monoclonal antibodies which are human or humanized antibodies using methods known in the art. As used herein, the term "antibody", refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Also, as used herein, "epitope" means a segment or feature of a protein capable of specific binding to an antibody. Also, as used herein, an "anti-interleukin antibody (AI-antibody)," "AI-antibody portion," or "AI-antibody fragment" and/or "AI-antibody variant" and the like include any protein or peptide containing molecule that comprises at least a portion of an immunoglobulin molecule, including, but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of an interleukin receptor (e.g. an IL-17 receptor) or binding protein, which can be incorporated into an antibody of the present invention. Such AI-antibodies optionally further affect a specific ligand, such as but not limited to where such an antibody modulates, decreases, increases, antagonizes, agonizes, mitigates, alleviates, blocks, inhibits, abrogates and/or interferes with at least one of a selected interleukins (e.g. IL-17a, IL-17b, etc.) activity or binding, or with IL-17 receptor activity or binding, in vitro, in situ and/or in vivo.

In various embodiments, the AI-antibodies described herein and incorporated into one or more embodiments of the microtablets or other shaped masses may correspond to any one of the Interleukin 1-36 family of interleukins along with their analogues and derivatives. In many embodiments, the invention provides shaped masses including a therapeutic composition comprising antibodies or other binding proteins to any one of the interleukin 1-36 family of interleukins (including their analogues and derivatives) which can be delivered into the wall of the small intestine or other target tissue site. This can be accomplished by incorporating or otherwise fabricating embodiments of the shaped mass into a biodegradable tissue penetrating member (e.g. in the form of a dart or needle) that is configured to be advanced into the small intestine by the application of mechanical force and biodegrade to release the IN-antibody into the intestinal wall and then the bloodstream. The tissue penetrating member may be contained and delivered from a swallowable capsule that includes means for insertion of the tissue penetrating member into the wall of the small intestine or other wall in the intestinal tract. Further description of the tissue penetrating member and swallowable capsule may be found in U.S. Pat. Nos. 8,721,620, 8,759,284 and U.S. patent application Ser. No. 13/532,589 which are incorporated herein for all purposes.

In specific embodiments, the invention provides mircrotablets or other shaped masses comprising antibodies which bind to members of the interleukin 17 family of antibodies, preferred examples including Secukinumab and Ixekizumab; and antibodies which bind to the receptor for the interleukin 17 family, a preferred example including Brodalumab, so as to prevent activation of the receptor by the antibody. Similar to TNF-antibodies these and other AI antibodies all have a disulphide bonds at the junction of their Y-shape which is the most labile part of the AI-antibody. As shown by the examples herein, the inventors have demonstrated (by virtue ELISA data showing that antibody molecule remain structurally intact and retains its bioactivity) that these disulphide bonds are preserved for various antibodies incorporated into a microtablet fabricated using the compression formation methods described herein. Therefore, one skilled in the art will appreciate that embodiments of the compression formation methods described herein would be expected to preserve the structure and bioactivity of these AI17 and other AI-antibodies. As such, particular embodiments of the invention provide shaped masses formed by compression or related method comprising AI-antibodies wherein 75, 80, 85, 90, 95% or more of the biological activity of the precursor AI-antibody material used to form the shaped mass is preserved in the final shaped mass.

AI-antibodies or other IN-protein provided by embodiments of the shaped masses herein are particularly useful for treating a number of autoimmune diseases and/or inflammatory conditions, including for example rheumatoid arthritis, psoriasis, plaque psoriasis, juvenile idiopathic arthritis, psoriatic arthritis, ankylosing spondylitis, multiple sclerosis, Crohn's disease, inflammatory bowel disease and ulcerative colitis. Such compositions result in the delivery of AI-antibody with desirable pharmacokinetic properties in particular pharmacokinetic properties which are advantageous verses intravenous, sub-dermal or intramuscular injection. They also allow for the usage of dosages which provide one or more of the following benefits including reduced incidence of allergic reaction including anaphylactic shock; and reduced immunogenicity (verses subcutaneous and/or intramuscular injection).

Anti-Interleukin-17 Antibodies

As discussed herein a number of embodiments of the invention provide shaped masses (e.g. microtablets, pellets, etc.) comprising AI-antibodies (or other IB-proteins) for neutralizing or otherwise inhibiting the biological effects of interleukins including those from the Interleukin 17 family of cytokines by preventing or modulating the ability of the antibody to attach to its selected receptor. These shaped masses may be configured to delivered to various target tissue sites in the body into the wall of the small intestine or other target tissue site in the intestinal tract. The targeted interleukin family of interleukin 17 antibodies include IL-17A, IL-17B, IL-17C, IL-17D, IL-17E (also called IL-25), and IL-17F. All members of the IL-17 family have a similar protein structure, with four highly conserved cysteine residues critical to their 3-dimensional shape, yet they have no sequence similarity to any other known cytokines. Numerous immune regulatory functions have been reported for the IL-17 family of cytokines, presumably due to their induction of many immune signaling molecules. The most notable role of IL-17 family of cytokines (also referred to as IL-17) is its involvement in inducing and mediating pro-inflammatory responses. IL-17 is commonly associated with allergic responses. IL-17 interleukins induce the production of many other cytokines (such as IL-6, G-CSF, GM-CSF, IL-β, TGF-β, TNF-α), chemokines (including IL-8, GRO-α, and MCP-1), and prostaglandins (e.g., PGE2) from many cell types (fibroblasts, endothelial cells, epithelial cells, keratinocytes, and macrophages). The release of cytokines causes many functions, such as airway remodeling, a characteristic of IL-17 responses. The increased expression of chemokines attracts other cells including neutrophils but not eosinophils. IL-17 function is also essential to a subset of $CD4^+$ T-Cells called T helper 17 (Th17) cells.

Owing to the above roles, the IL-17 family of interleukins has been linked or otherwise associated with many immune/autoimmune related diseases including for example, rheumatoid arthritis, psoriatic arthritis, asthma, lupus, allograft rejection, anti-tumor immunity and recently psoriasis and plaque psoriasis. In particular, increased expression of three of the IL-17 subtypes (A, C and F) has been implicated in the pathogenesis of inflammation in psoriasis. Accordingly, embodiments of the invention providing shaped masses having a therapeutic composition comprising antibodies to one or more IL-17 interleukins or receptors to the interleukin-17 family of interleukins, (herein Anti-IL-17 antibodies or AI17-antibodies) are useful for treating one or more of these and other immune/autoimmune conditions. This is particularly the case for embodiments of the shaped masses that are used to deliver the AI17-antibodies into the walls of the small intestine (or other target site in the intestinal tract) as this allows for improved pharmacokinetics and reduced allergic and other adverse reactions when the antibodies are delivered by IV, intramuscular or other form of injection. Again, the AI17-antibodies can be configured to attach to the interleukin itself or the receptor to the interleukin thus preventing the receptor from being activated by the interleukin and in turn inhibiting otherwise attenuating the biologic effect of such activation. The inhibited or attenuated biological effects may include one or more of the following: Th1 modulation; Th2 modulation (Nakanishi K., et al. (2001) Cytokine and Growth Factor Rev. 12:53-72); and NK modulation. Various embodiments of specific AI17-antibodies are discussed in further detail below.

Secukinumab

Secukinumab is a human monoclonal antibody (mAb) that selectively binds to and inhibits and/or neutralizes the activity of interleukin-17A (IL-17A) which has been implicated in a number of immune/autoimmune related conditions including plaque psoriasis. It is the first IL-17A inhibitor approved by the FDA for the treatment of moderate-to-severe plaque psoriasis in adult patients who are candidates for systemic therapy. It has also shown positive clinical results for the treatment of ankylosing spondylitis, psoriatic arthritis and is being evaluated for the treatment of multiple sclerosis and rheumatoid arthritis. Accordingly, various embodiments of the invention contemplate the delivery of shaped masses comprising therapeutically effective amounts of Secukinumab into the walls of the small intestine (or other target tissue site in the intestinal tract or other location) for the treatment of one or more of the following conditions: psoriasis including plaque psoriasis, ankylosing spondylitis, psoriatic arthritis, multiple sclerosis, rheumatoid arthritis. The doses of Secukinumab for such treatment can be in a range from about 1-40 mg per day (which can be delivered by means of the tissue penetrating member described herein) with a specific dose range of about 20-40 mg per day for the treatment of plaque psoriasis. For these and other dosages, the daily dose may be initiated after a loading dose which may administered via injection (e.g. IV, intramuscular or subdermal) or other delivery method. The dose may be titrated for an individual patient based on one or more of the patient's, weight, age, severity of condition, amount of the loading dose and treatment efficacy index known in the art for a given condition, for example, Psoriasis Area and Severity Index (PASI) and Investigator's Global Assessment modified 2011 (IGA) for the treatment of plaque psoriasis. Further description of Secukinab including formulations, doses and clinical uses may be found in U.S. patent application Ser. Nos. 13/876,367, 13/877,585 and 14/358,504 which are incorporated by reference herein in their entirety for all purposes.

Brodalumab

Brodalumab is a human monoclonal antibody (mAb) that binds with high affinity to the receptor for and inhibits and/or neutralizes the activity interleukin-of 17A (IL-17A) a molecule which, as indicated above, has been implicated in a number of immune/autoimmune related conditions including plaque psoriasis. Brodalumab is the only investigational treatment in development that binds to the interleukin-17 (IL-17) receptor and inhibits inflammatory signaling by blocking the binding of several IL-17 cytokines (e.g. A, F and A/F) to the receptor. As such, it would have efficacy for the treatment of any condition involving the activation of one or more of these receptors including without limitation, one or more of plaque psoriasis, ankylosing spondylitis, psoriatic arthritis, multiple sclerosis, rheumatoid arthritis and inflammatory bowel disease. It has also shown positive clinical results in a phase 3 study for the treatment of plaque psoriasis. Accordingly, various embodiments contemplate the delivery of shaped masses (e.g, microtablet) comprising therapeutically effective amounts of Brodalumab into the walls of the small intestine (or other target tissue site in the intestinal tract or other location) for the treatment of one or more of the following conditions: psoriasis including plaque psoriasis, ankylosing spondylitis, psoriatic arthritis multiple sclerosis, rheumatoid arthritis, inflammatory bowel disease and other like conditions. The doses of Brodalumab for such treatment (which can be delivered by means of embodiments of the tissue penetrating member described herein) can be in a range from about 1-20 mg per day with a specific dose range of about 9-14 mg per day for the treatment of plaque psoriasis. For these and other dosages, the daily dose may be initiated after a loading dose which may administered via injection or other delivery means. The dose may be titrated for an individual patient based on one or more of the patient's, weight, age, severity of condition, amount of the loading dose and treatment efficacy index known in the art for a given condition for example Psoriasis Area and Severity Index (PASI) and Investigator's Global Assessment modified 2011 (IGA) for the treatment of plaque psoriasis. Further description of Brodalumab including doses and clinical uses may be found in the paper by Coimbra, et al. entitled, "Brodalumab: an evidence-based review of its potential in the treatment of moderate-to-severe psoriasis" Core Evid. 2014 Jul. 21; 9:89-97 which is incorporated by reference herein for all purposes.

Ixekizumab

Ixekizumab is a human monoclonal antibody (mAb) that selectively binds to and inhibits and/or neutralizes the activity of interleukin-17A (IL-17A) which has been implicated in a number of immune/autoimmune related conditions. It has also shown positive clinical results for the treatment of psoriatic arthritis and plaque psoriasis. Accordingly, various embodiments contemplate the delivery of shaped masses comprising therapeutically effective amounts of Brodalumab Ixekizumab into the walls of the small intestine (or other target tissue site in the intestinal tract or other location) for the treatment of one or more of the following conditions: psoriasis including plaque psoriasis, ankylosing spondylitis, psoriatic arthritis, multiple sclerosis and rheumatoid arthritis. The doses of Ixekizumab for such treatment (which can be delivered by embodiments of the tissue penetrating member described herein) can be in a range from about 1-40 mg per day (which can be delivered by means of one or more swallowable capsule or multiple capsules given over the course of the day) with a specific dose range of about 2.5-5.5 mg per day for the treatment of psoriatic arthritis or plaque psoriasis. For these and other dosages, the daily dose may be initiated after a loading dose which may administered via injection or other delivery means. The dose may be titrated for an individual patient based on one or more of the patient's, weight, age, severity of condition, amount of the loading dose and treatment efficacy index known in the art for a given condition for example Psoriasis Area and Severity Index (PASI) and Investigator's Global Assessment modified 2011 (IGA) for the treatment of plaque psoriasis. Further description of Ixekizumab including formulations, doses and clinical uses may be found in U.S. patent application Ser. No. 14/195,885 which is incorporated by reference herein in its entirety for all purposes.

Benefits of Delivery of AI17-Antibodies into the Intestinal Wall or Other Location in the Intestinal tract.

In use, embodiments of the invention providing for delivery of Secukinumab, Broadulmab, Ixekizumab or other AI-antibody or IN-protein by means of solid shaped masses into the wall of the small intestine (or other target site in the intestinal tract) for treatment of one or more of immune/autoimmune conditions described herein or known in the medical field provide a number of benefits over injected forms of AI-17-Antibodies (e.g., Secikinumab). These can include a higher therapeutic ratio, reduced incidence and severity of the adverse reactions including one or more of: anaphylactic shock or other allergic reaction (including at the injection site); and nasopharyngitis, upper respiratory tract infection, and headache (the latter three being noted from clinical studies for one or more of Secukinumab, Broadulmab, or Ixekizumab) and decreased immungenicity and/or immunogenetic reaction. In the later case, such immunogenic reactions can result in the development in the patient of antibodies to the AI17 antibodies themselves resulting in reduced efficacy and the requirement of higher doses of drug and/or an unwanted immune response. These benefits are due to one or more of the following: i) the much smaller doses of AI17-antibodies or (or other AI-antibody or IN-protein) that are delivered by embodiments of the invention; ii) doses are delivered daily vs weekly or monthly; and iii) the fact that doses are delivered orally vs intravascularly.

In many embodiments, the therapeutic ratio of dosages of AI17-antibodies delivered orally by embodiments of the shaped masses can be increased significantly over that for AI17-antibody(s) delivered by injection (e.g., intravenously, intramuscularly, or subcutaneously, etc on a weekly, biweekly, or monthly basis). In various embodiments, the term "significantly" corresponds to an increase in the therapeutic ratio in an amount of two times or greater, e.g, seven to thirty times greater or more. For AI17-antibodies or (or other AI-antibody or IN-protein) that are typically delivered in weekly doses when injected (e.g instravenously, intramuscularly, or subcutaneously, etc), the therapeutic ratio (e.g Toxic Dose/Effective Dose) can be increased by a factor of seven when delivered in daily oral doses using embodiments of the shaped masses/tissue penetrating member described into the walls of the small intestine, while in the case of monthly injected doses of AI17 antibodies the therapeutic ratio can be increased by a factor of 30 when delivered daily oral doses by embodiments of the invention. Further, increases can be obtained when the oral dose of AI17-antibody is given multiple times over a day. Similar improvements (e.g by a factor of 7, 30 or even more) can seen in the incidence in one or more of immunogenicity/immune response (vs intramuscular and/or subcutaneous injection), allergic reaction, and other adverse reactions. Immunogenicity/immune response, being the production by the body of antibodies to the administered to the AI17-antibody which neutralize or otherwise diminish the clinical efficacy of the AI17-antibody. The reduction in the incidence of allergic reaction can be by a factor of two up to 30 due to the fact that the antibodies are given in daily doses vs monthly doses which tends to desensitize the immune system (the degree of allergic reaction can be determined using methods known in the art and may be correlated to one or more in vitro tests known in the art). Similarly, the degree of reduced immunogenicity and/or immune response can be by a factor of two to as much as thirty or more due three possible factors: 1) the doses are not delivered subcutaneously and/or intramuscularly (which tend to exacerbate such responses); 2) the doses are delivered in much smaller amounts, e.g by a factor of 7 to as much as 30 depending on whether the injected dose is delivered weekly, biweekly, monthly etc; and 3) as discussed above the dose AI-17 antibody is delivered to the upper portions of the small intestine avoiding the peyer's patches and subsequent production of immune cells and other immune response. The amount of immune response to a given AI17-antibody (e.g., Secukinumab) can be quantified using one more immunologic analytical methods known in the art to measure for example the production of generated antibodies to the delivered AI17-antibody or other AI-antibody. In particular embodiments, the dosage of AI17-antibody can be configured to yield a minimal amount of antibodies to the AI17-antibody in the patient, wherein minimal means less than 10% of the delivered AI17-antibodies are neutralized by the patient's own antibodies and more preferably less than 5%.

Embodiments of Shaped Massed Produced Using 3-D Printing.

Still other embodiments of the invention provide methods of preparing a shaped mass comprising a drug (which may comprise a protein or polypeptide) wherein an outer coating(s) and/jacket of materials is formed over the drug using 3-D printing methods so as to form a selectively shaped micro-micro tablet or other shaped mass. The coating or jacket may comprise one more biodegradable materials described herein. According to one or more embodiments, the 3-D printing methods can be configured to deposit the coating or jacket as a single layer or as a multilayer coating. In the latter case, different layers can be applied which have different compositions, material properties, and thicknesses. In use, such multilayer applications allow for more precise control of one or more properties of the shaped mass including for example the rates of biodegradation of the shaped mass. For example, according to one embodiment, a relatively fast degrading layer can be deposited over a drug layer, which is in turn positioned over a more slowly degrading layer that in turn is positioned over a core mass of drug. In use, such embodiments can provide for a bio-modal form of release with a rapid release (e.g., a bolus release) of drug under the first layer and a more slow release of drug under the second layer.

Use of 3-D printing methods allow the shaped mass to be formed with minimal or no pressure applied to the mass and in turn the underlying drug. In use, such methods improve the yield of the drug in the final shaped mass due to decreased protein denaturation and/or other degradative effects on the drug. This in turn improves the bioactivity of the drug in the final shaped mass. Use of 3-printing also allows a variety of shapes to be produced without use of a mold or other related device reducing the potential for contamination and improving sterility. Such shapes may include for example, an arrow head shape (e.g. the embodiment of FIG. 8) rectangle, pyramidal, spherical, hemispherical, conical and others as is shown in FIGS. 1-10. 3 D printing methods also allow for rapid customization of the drug mass shape and size for individual patient parameters, for example, one or more of a patient's weight, medical condition and particular medical regimen (e.g. taking of medication once day, twice etc.). In still other embodiments, 3-D printing methods can be used to produce shaped masses configured to have a bimodal form of delivery, e.g. fast release and slow release.

Embodiments of Inventories of Shaped Masses Having Uniform Properties.

Other embodiments of the invention provide an inventory of shaped masses comprising a drug such as a peptide, protein or immunoglobulin, wherein a property of the shaped mass and/or the drug, such as the biological activity of the drug post formation, is maintained within a selected range for substantially the entire inventory. In use, such embodiments, help to ensure the uniformity of one more of dosage, pharmacokinetic parameters (e.g. $t_{1/2}$, $t_{max}$, $C_{max}$, etc.) and resulting clinical effect for one or more selected drugs delivered using the shaped masses. For example, for embodiments of the shaped mass comprising insulin, the biological activity and/or weight percentage of the insulin post formation can be maintained in a range of about 99.2 to 99.8% to that prior to formation for substantially the entire inventory.

Routes of Delivery for the Shaped Masses. Embodiments of the micro-tablets or other shaped massed described herein, can be configured to be used in combination with any suitable drug delivery system to be administered via any appropriate route of administration. Such routes of administration can include without limitation, oral, sublingual parenteral, intravenous, intramuscular, subcutaneous, intraventricular, intra-cardiac, intra-cerebral. For example, according to one embodiment, insulin comprising micro-tablets can be taken orally and then have the drug be absorbed through the wall of the small intestine or delivered into the wall small intestine. In the latter case, this can be done using a drug delivery device which includes a biodegradable tissue penetrating member which contains or otherwise includes the microtablet. The tissue penetrating member may be advanced into the intestinal wall using an advancement means such as an inflatable balloon which directly or indirectly applies a force to the tissue penetrating member. In an alternative or additional embodiment, the micro-tablet can be delivered subcutaneously to an intramuscular or other subcutaneous tissue site. In specific embodiments, the micro-pellet can be configured to dissolve at a selectable rate or rates to achieve a $C_{max}$ or other desired pharmacokinetic parameter (e.g. $t_{max}$ etc.). Further, the composition and properties of the micro-tablet can be configured have a dissolution rate configured to achieve the desired $C_{max}$ for the tissue at a given site (e.g. in the wall of the small intestine, vs an intramuscular site). In particular embodiments, the shaped mass can be inserted into a cavity in the tissue penetrating member which is then sealed up. The tissue penetrating member may comprise any number of biodegradable materials such as maltose, sucrose or other sugar, PGLA (Polyglycolic lactic acid), polyethylene and others as is described in more detail above.

EXAMPLES

Various embodiments of the invention are further illustrated with reference to the following examples. It should be appreciated that these examples are presented for purposes of illustration only and that the invention is not to be limited to the information or the details therein.

Example 1: Micro-Tablets Comprising Human IgG and PEG

Materials.

Pure human IgG (Alpha Diagnostics Intl. Inc, Cat #20007-1-100), Poly Ethylene Glycol 3350 (PEG, Sigma-Aldrich, Cat #P4338-500G), Water, molecular biology reagent grade (Sigma-Aldrich, Cat #W4502).

Methods.

Human IgG and PEG 3350 in powder form were weighed out and mixed into a solution using molecular biology reagent grade water. The percentage of IgG and PEG are 90% and 10% respectively and the powders were dissolved in water at 40 mg/ml concentration. Batches using different IgG mass capacity were prepared: 100 mg (batch 6 and 7), 140 mg (batch 8) and 60 mg of IgG (batch 9). The aqueous solution was placed in a silicone plate and then evaporated in a vacuum chamber with desiccant inside of a refrigerator for a minimum of 19 hours (batch 6, 7 and 8) and up to 21 hours (batch 9) until full evaporation occurs. Data for batches 1-5 are not included because these batches were trial batches made using a different processes (e.g. different or no milling, evaporation, etc.) and micro-tablets were not fabricated for some of these batches as well.

The evaporated powder was collected into a low-bind conical 1.5 ml tube. Two small stainless steel balls (3.96 mm diameter, 0.5 g total mass) and a rotator (Roto-shake Genie) at max speed were used for milling. The milling duration was 1.75 hrs (batches 6 and 7) and 1.5 hours (batches 8 and 9). It was done at 64° F. room temperature with an ice pack surrounding the tube Once the powder was milled, microtablets were fabricated using a semiautomatic molding fixture. The molding parameter included a compressive force of approximately 2.5 to about 3.5 lbs of force and a compression hold time of approximately 3 sec. Measurements were made of the amount of intact (e.g. biological active) IgG that was recovered in the powder from before-milling, after-milling and in the formed micro-tablets. These measurements were made using IgG immunoassay (Alpha Diagnostics Inc.).

Micro-tableting includes the steps of processing of the powder recovered from evaporation into fine homogenous powder and then forming it into a solid microtablet. The before-milling powder recovery is the starting point of the microtableting process and the percentage of IgG recovered using this manufacturing method was calculated by taking the before-milling protein recovery (e.g., the amount of biologically protein active recovered in the powder prior to milling) to be 100%. The microtablet data and IgG recovery values are detailed in Table 1. Densities were measure by measuring the mass and volume of the tablet. Average density was found to be between 1.02 and 1.06 mg/mm$^3$ while the recovery of intact and bioactive IgG found in the microtablets was equal or higher than 94.2% in average.

TABLE 1

Microtablet Data and IgG Recoveries for IgG Microtablets Comprising 90% IgG and 10% PEG 3350

| IgG Batch #* | Microtablet Length (mm) | Microtablet Weight (mg) | Microtablet Density (mg/mm$^3$) | Absolute Microtablet IgG Recovery |
|---|---|---|---|---|
| 6 | 2.77 ± 0.07 (N = 23) | 1.16 ± 0.03 (N = 23) | 1.05 ± 0.01 (N = 23) | 87% ± 1.4% (N = 10) |

TABLE 1-continued

Microtablet Data and IgG Recoveries for IgG Microtablets Comprising 90% IgG and 10% PEG 3350

| IgG Batch #* | Microtablet Length (mm) | Microtablet Weight (mg) | Microtablet Density (mg/mm³) | Absolute Microtablet IgG Recovery |
|---|---|---|---|---|
| 7 | 3.17 ± 0.15 (N = 15) | 1.33 ± 0.06 (N = 15) | 1.06 ± 0.02 (N = 15) | 94.1% ± 0.9% (N = 5) |
| 8 | 2.67 ± 0.09 (N = 15) | 1.11 ± 0.03 (N = 15) | 1.06 ± 0.02 (N = 15) | 89.2% ± 3.2% (N = 5) |
| 9 | 2.85 ± 0.09 (N = 13) | 1.15 ± 0.02 (N = 13) | 1.02 ± 0.02 (N = 13) | 77.8% ± 1.6% (N = 4) |

Example 2: Micro-Tablets Comprising Human IgG PEG and Other Excipients

Materials.

Pure human IgG (Alpha Diagnostics Intl. Inc, Cat #20007-1-100), Poly Ethylene Glycol 3350 (PEG, Sigma-Aldrich, Cat #P4338-500G), Water, molecular biology reagent grade (Sigma-Aldrich, Cat #W4502), sodium chloride (Sigma-Aldrich, Cat #S9888), mannitol (Sigma-Aldrich, Cat #M8429-100G).

Methods.

Human IgG was dissolved along with lubricant PEG 3350 and principal excipients in HUMIRA pen (sodium chloride and mannitol) in the same percentage that in the pen solution. The powders were brought into solution using 0.94 ml of molecular biology reagent grade water. The evaporation process was done using the same procedure as used in a) above.

The evaporated powder was then transferred to a low-bind round-bottom 2 ml tube. The milling process was slightly different for each batch. Batches 7 and 8 were milled using stainless steel ball having a mass of 0.438 with 3 hours of milling. Batch nine was made using a 9 an Yttrium-stabilized zirconium ball having a mass of 0.454 with a milling duration of 3 hours. The rotation method and temperature conditions were kept as used in example 1). Note, data for batches 1-6 are not included because they were made for milling optimization purposes only and micro-tablets were not fabricated for these batches. Approximate measurements were made of particle grain sizes (diameter or widest dimension) for cases 7, 8 and 9 using a hemocytometer. Particle size ranged from about 50 to about 450 μm for the three batches with specific data of 100, 200, 200, 400 and 400 for batch 7; 50, 200, 300 and 400 for batch 8; and 50, 100, 300 and 450 for Batch 9.

After milling, micro-tablets were fabricated using an automatic fixture using compression forces 2.6 lbs of compression force and a compression holding time of 3 sec. The intact IgG recovered from the stages of before-milling powder, after-milling powder and microtablets were tested using an IgG immunoassay (Alpha Diagnostics Inc.). The microtablet data and IgG recovery values are detailed in Table 2.

Definitions for terms used in Tables: The definitions for the terms used in the tables below is provided below.

Absolute protein recovery after micro-tableting (APRAMT): This is the percentage of active protein in the micro-tablet relative to that amount in the powder used to form the micro-tablet. It determined using an ELISA assay of the selected protein in the micro-tablet. The formula for calculation of this value is shown below APRAMT=(ELISA estimated protein content mass in the microtablet)/(total microtablet mass*protein mass percentage in total mass)

TABLE 2

Microtablet Data and IgG recoveries in IgG Microtablet

| | | | Formulation | | | |
|---|---|---|---|---|---|---|
| | | 67.8% IgG | 7.5% PEG 3350 | 8.4% NaCl | 16.3% Mannitol | |
| IgG Batch # | Milling Ball | Ball Mass (grams) | Microtablet Length (mm) | Microtablet Weight (mg) | Microtablet Density (mg/mm³) | Absolute Microtablet IgG Recovery |
| 7 | 1 S. Steel | 0.438 | 3.23 ± 0.15 (N = 8) | 1.25 ± 0.07 (N = 8) | 0.97 ± 0.01 (N = 8) | 89.3% (N = 2) |
| 8 | 1 S. Steel | 0.438 | 2.5 ± 0.21 (N = 5) | 1.1 ± 0.07 (N = 5) | 1.12 ± 0.02 (N = 5) | 96% (N = 2) |
| 9 | 1 Zirconium | 0.4539 | 2.76 ± 0.14 (N = 5) | 1.29 ± 0.05 (N = 5) | 1.18 ± 0.01 (N = 5) | 94% (N = 2) |

Example 3: Micro-tablets Comprising HUMIRA and HUMIRA Pen Excipients

Materials.

HUMIRA pens (Abbott Laboratories) and Poly Ethylene Glycol 3350 (PEG, Sigma-Aldrich, Cat #P4338-500G).

Methods.

The solution contained in the HUMIRA pen was placed in a low-bind 1.5 ml tube where PEG 3350 amount was added and mixed with HUMIRA ingredients. The solution was evaporated following the same conditions as the ones described in example 1 a) and b).

The milling conditions were the same as in example 1 a) where two balls were used with total mass of 0.5 grams and 1.5 hours (batch 1, 2 and 4) and 1.75 hours (batch 3) of milling duration. The same temperature conditions were kept as in example 1.

After powder milling, microtablets were formed by using a semiautomatic fixture using approx. 3 lbs. of force for compression and a holding compression time of approx. 3 sec. The intact HUMIRA recovered in before-milling powder, after-milling powder and microtablets were tested using an HUMIRA immunoassay (Alpha Diagnostics Inc.). As in example 1), the before-milling powder recovery is the starting point of the microtableting process and the percentage of HUMIRA recovered using this manufacturing method was calculated using the before-milling powder recovery as 100%. The microtablet data and HUMIRA recovery values are detailed in Table 3.

The average density ranged from about 0.88 up to about 1.05 mg/mm$^3$ and the amount of bioactive HUMIRA recovered in the microtablets ranged from about 67 to about 80% to that prior to formation of the microtablet.

TABLE 3

Microtablet Data and Adalimumab recoveries in Adalimumab Microtablet Formulation: 90% HUMIRA Preparation (Drug and Excipients) from HUMIRA Pen

| Batch | Adalimumab Amount (mg) | PEG added (mg) | Microtablet Length (mm) | Microtablet Weight (mg) | Microtablet Density (mg/mm$^3$) | Absolute Microtablet Adalimumab Recovery |
|---|---|---|---|---|---|---|
| 1 | 40 | 4.4 | 3.28 ± 0.16 (N = 19) | 1.33 ± 0.05 (N = 19) | 1.03 ± 0.02 (N = 19) | 79.3% ± 2.3% (N = 6) |
| 2 | 40 | 4.4 | 4.12 ± 0.17 (N = 13) | 1.56 ± 0.08 (N = 13) | 0.96 ± 0.03 (N = 13) | 74% (N = 2) |
| 3 | 40 | 4.4 | 3.15 ± 0.03 (N = 23) | 1.22 ± 0.02 (N = 23) | 0.98 ± 0.01 (N = 23) | 66.7% (N = 2) |
| 4 | 48 | 5.3 | 3.25 ± 0.1 (N = 23) | 1.13 ± 0.04 (N = 23) | 0.88 ± 0.02 (N = 23) | 76.2% ± 2% (N = 9) |

Example 4: Micro-tablets Comprising Insulin-Biotin Complex

Materials.

Biotin-Human Insulin solution (Alpha Diagnostics, cat #INSL16-BTN-B) and Poly Ethylene Glycol 3350 (PEG, Spectrum, Cat #P0125-500G).

Methods.

Biotinylated insulin (insulin with an attached biotin molecule) was purchased from Alpha Diagnostics and received in a liquid form containing 2 mg/ml Insulin in 1×PBS (12 mM KPO4, 2.7 mM KCl, and 137 mM NaCl, pH 7.4). Ovalbumin was added to the solution at 1% by supplier. The solution purchased was placed in a low-bind 1.5 ml tube where PEG 3350 was added and mixed and mixed into the solution. The constituency of the final formulation for bathes 4-7 was the following: 8.7% biotin-human insulin complex, 5% PEG 3350, 43.5% Ovalbumin and 42.7% salts from 1×PBS during dialysis. Note batches, 1-3, were not included here due to large difference in the excipients amounts from batches 4-5. The solution was evaporated following the same conditions as the ones described in example 1.

Once the powder was fully dry, it was then transferred to a low-bind round-bottom 2 ml tube. The milling process used a single Yttrium-stabilized zirconium ball having a mass of 0.445 g for duration of 1.5 hours. The rotation method and temperature conditions were the same as used in Example 1.

After milling, microtablets were fabricated using an automatic fixture using 26 psi air pressure for compression, resulting in a compression force of about 1.8 lbs, and using a holding compression time of 3 sec. The air pressure for ejection was set at 28 psi (~1.82 lbs ejection force). The Biotin-Human Insulin microtablets were tested using an Insulin-biotin ELISA immunoassay kit (Alpha Diagnostics Inc., Cat #0030-20-1). The microtablet data and Biotin-Human Insulin recovery values are listed in Table 4.

TABLE 4

Microtablet Data and Biotin-Human Insulin Complex Recovery Data

| Formulation | 8.7% Biotin-Human Insulin Complex | 5% PEG 3350 | 43.5% Ovalbumin | 42.7% Salts from IX PBS during dialysis |
|---|---|---|---|---|

| Batch | Microtablet Length (mm) | Microtablet Weight (mg) | Microtablet Density (mg/mm$^3$) | Absolute Microtablet Insulin Recovery |
|---|---|---|---|---|
| 4 | 3.4 ± 0.07 (N = 4) | 1.35 ± 0.08 (N = 4) | 1 ± 0.05 (N = 4) | 94.2% ± 3.6% (N = 3) |
| 5 | 3.78 ± 0.04 (N = 5) | 1.35 ± 0.02 (N = 5) | 0.9 ± 0.01 (N = 5) | 69.9% ± 2.3% (N = 3) |

Example 5: Micro-tablets Comprising Insulin

Materials.

Human Insulin (Imgenex, cat #IMR-232-250), Poly Ethylene Glycol 3350 (PEG, Spectrum, Cat #P0125-500G), Mannitol (Amresco, Cat #0122-500G), Povidone (ISP-Technologies, Plasdone C-30) and sterile water (APP Pharmaceutical, Cat #918510).

Methods.

Human insulin was mixed in solution with different excipients producing various batches for analysis. The formulation of each batch is detailed in Table 5. Batches 1-A, 2, 3B and 6B were not included due to different fabrication parameters. The excipients included PEG 3350 (lubricant), Mannitol (bulking agent) and Povidone (binder). These excipients and the API (human insulin) were dissolved in sterile water. The solution was evaporated using the same conditions as the ones described in example 1.

The milling process and parameters were the same as in example 4, using a low-bind round-bottom 2 ml tube and a single Yttrium-stabilized zirconium ball (mass of approx. 0.45 g) for duration of 1.5 hours. The rotation method and temperature conditions were kept as used in Example 1.

After milling, microtablets were fabricated using an automatic fixture with 74.5 psi air pressure used for compression (resulting in a compression force of about 2.6 lbs) and a holding compression time of 3 sec. The air pressure for ejection was set at 80 psi (~2.7 lbs ejection force) The human Insulin microtablets were tested using Human Insulin ELISA immunoassay kit (Alpha Diagnostics Inc., Cat #0030N). The microtablet data and Human Insulin recovery values are detailed in Table 6.

TABLE 5

Formulation for Human Insulin Microtablets (weight %)*

| Batch | Human Insulin | PEG 3350 | Mannitol | Povidone |
|---|---|---|---|---|
| 1B | 25.8% | 5% | 69.2% | — |
| 3A | 23% | 5% | 72% | — |
| 4 | 89% | 5% | 6% | — |
| 5 | 89% | 5% | 4% | 2% |
| 6A | 80% | 5% | 13% | 2% |
| 7 | 80% | 5% | 13% | 2% |

*Note, the formulation are listed for Insulin batches 1b-7 because the composition in these batches changed batch to batch, they did not do so for other batches.

TABLE 6

Microtablet Data and Human Insulin Recovery Data

| Batch | Microtablet Length (mm) | Microtablet Weight (mg) | Microtablet Density (mg/mm$^3$) | Absolute Microtablet Insulin Recovery |
|---|---|---|---|---|
| 1B | 2.1 ± 0.03 (N = 22) | 0.9 ± 0.01 (N = 22) | 1.08 ± 0.01 (N = 22) | 87.5% ± 0.8% (N = 5) |
| 3A | 2.32 ± 0.07 (N = 6) | 0.93 ± 0.02 (N = 6) | 1.01 ± 0.01 (N = 6) | 96.6% ± 2.6% (N = 3) |
| 4 | 2.42 ± 0.11 (N = 5) | 0.97 ± 0.04 (N = 5) | 1.01 ± 0.01 (N = 5) | 81.1% ± 3.1% (N = 3) |
| 5 | 2.42 ± 0.07 (N = 9) | 0.95 ± 0.02 (N = 9) | 0.99 ± 0.02 (N = 9) | 97.6% ± 1.6% (N = 6) |
| 6A | 1.95 ± 0.03 (N = 15) | 0.86 ± 0.01 (N = 15) | 1.12 ± 0.01 (N = 15) | 94.8% ± 3.5% (N = 3) |
| 7 | 2.09 ± 0.02 (N = 82) | 0.91 ± 0.01 (N = 82) | 1.09 ± 0.01 (N = 82) | 99.5% ± 0.3% (N = 16) |

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Further, various embodiments expressly contemplate the negative recitation of any element that shown or described in one or more embodiments. Hence, the scope of the present invention is not limited to the specifics of the described embodiments, but is instead limited solely by the appended claims.

What is claimed is:

1. A shaped mass comprising an immunoglobulin G (IgG), the shaped mass comprising the IgG, wherein at least about 67% of the IgG in the shaped mass has affinity for an antigen, the shaped mass having a density in a range of about 0.80 to about 1.10 mg/mm$^3$.

2. The shaped mass of claim 1, wherein the density is in a range of about 1.00 to about 1.01 mg/mm$^3$.

3. The shaped mass of claim 1, wherein a precursor material to the shaped mass has a particle size in a range of about 50 to about 450 µm.

4. The shaped mass of claim 1, wherein the compression is performed in a mold or fixture.

5. The shaped mass of claim 1, wherein the shaped mass is formed by compression of a powder comprising the IgG.

6. The shaped mass of claim 1, wherein the shaped mass has a pellet or cylindrical shape.

7. The shaped mass of claim 1, wherein the shaped mass has a tablet shape.

8. The shaped mass of claim 1, wherein the shaped mass has a tissue penetrating shape.

9. The shaped mass of claim 1, wherein the shaped mass comprises a biodegradable material said biodegradable material configured to breakdown in a wall of a small intestine so as to release the IgG.

10. The shaped mass of claim 1, wherein the shaped mass comprises a pharmaceutical excipient.

11. The shaped mass of claim 10, wherein the pharmaceutical excipient comprises at least one of a lubricant, a binding agent or a bulking agent.

12. A shaped mass comprising an immunoglobulin G (IgG), the shaped mass comprising the IgG, wherein at least about 67% of the IgG in the shaped mass has affinity for an antigen, and wherein a precursor material of the shaped mass has a particle size in the range of 50 to 450 µm.

13. The shaped mass of claim 12, wherein the precursor material has a particle size in the range of 100 to 400 µm.

14. The shaped mass of claim 12, wherein the compression is performed in a mold or fixture.

15. The shaped mass of claim 12, wherein the shaped mass is formed by compression of a powder comprising the IgG.

16. The shaped mass of claim 12, wherein the shaped mass has a cylindrical or pellet shape.

17. The shaped mass of claim 12, wherein the shaped mass has a tablet shape.

18. The shaped mass of claim 12, wherein the shaped mass has a tissue penetrating shape.

19. The shaped mass of claim 12, wherein the shaped mass comprises a biodegradable material said biodegradable material configured to breakdown in a wall of a small intestine so as to release the immunoglobulin G.

20. The shaped mass of claim 12, wherein the shaped mass comprises a pharmaceutical excipient.

21. The shaped mass of claim 20, wherein the pharmaceutical excipient comprises at least one of a lubricant, a binding agent or a bulking agent.

* * * * *